US00PP09008P

United States Patent [19]

Austin

[11] Patent Number: Plant 9,008

[45] Date of Patent: Dec. 13, 1994

[54] SHRUB ROSE PLANT NAMED AUSPOLY

[75] Inventor: David C. H. Austin, Albrighton, England

[73] Assignee: David Austin Roses Limited, Albrighton, England

[21] Appl. No.: 182,783

[22] Filed: Jan. 13, 1994

[51] Int. Cl.[5] ..... A01H 5/00

[52] U.S. Cl. ..... Plt./1

[58] Field of Search ..... Plt. 1, 24

U.S. PATENT DOCUMENTS

PLT 8682 4/1994 Austin .....PLT/1

PLT 8688 4/1994 Austin .....PLT/1

*Primary Examiner*—Howard J. Locker

*Attorney, Agent, or Firm*—Klarquist Sparkman Campbell Leigh & Whinston

[57] ABSTRACT

A shrub rose having full, double, orange/yellow flowers, repeat flowering, and bushy growth.

1 Drawing Sheet

The present invention relates to a new and distinct variety of rose plant of the shrub class which was originated by me by crossing an unnamed seedling with the variety "Graham Thomas."

The primary objective of this breeding was to produce a new shrub rose variety that is repeat-flowering and has yellow, old-fashioned-shaped flowers. The objective was substantially achieved, along with other desirable improvements, as evidenced by the following unique combination of characteristics that are outstanding in the new variety and that distinguish it from its parents, as well as from all other varieties of which I am aware:

1. Orange/yellow flowers;
2. Repeat flowering;
3. Full, double flowers; and
4. Bushy growth.

Asexual reproduction of this new variety by budding, as performed at Albrighton, Wolverhampton, England, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed seedling.

*Pollen parent.*—"Graham Thomas" (unpatented).

Classification:

*Botanical.*—Rosa hybrida.

*Commercial.*—Shrub.

FLOWER

Observations made from specimens grown in a garden environment at Albrighton, Wolverhampton, England in Jul. 1992.

Blooming habit: Recurrent.

Bud:

*Size.*—2.5 to 3.0 cm long when the petals start to unfurl.

*Form.*—The bud form is pointed ovoid.

*Color.*—When sepals first divide, bud color is Yellow-Orange Group 14C/D. When half blown, the upper sides of the petals are Yellow-Orange Group 14D at the base, with Yellow-Orange Group 14B/C to Yellow Group 13D at the top edge; and the lower sides of the petals are Yellow-Orange Group 16B at the center, fading through Yellow-Orange Group 16C and 16D at the top edge.

*Sepals.*—Color: Green group 143C with deep pink blush. Surface texture: Leathery, slightly puckered. There are three appendaged sepals. There are two unappendaged sepals with downy edges.

*Receptacle.*—Color: Green Group 143C. Shape: Narrow goblet shaped. Size: Slender, about 12 to 14 mm long ×8 to 9 mm wide.

*Peduncle.—Surface: Smooth. Length: Averaging about* 3.5 to 4.0 cm. Surface: Glandular. Color: Light to medium green. Strength: Erect, slender.

Bloom:

*Size.*—Average open diameter is 8.0 cm.

*Borne.*—In irregularly shaped clusters of 3 to 9 blooms.

*Stem.*—Average length is about 75 to 80 cm; normal strength.

*Form.*—When first open: Deeply cupped. Permanence: Flattens somewhat. Outer petal edges curl slightly.

*Petalage.*—Number of petals under normal conditions: about 100.

*Color.*—The upper side of the petals is Yellow Group 13C, deepening to Yellow Group 13B toward base. The reverse side of the petals is Yellow-Orange Group 14C. The base of each petal has a Yellow-Orange Group 14A/B tip. The major color on the upper side is Yellow Group 13C.

*Variegations.*—None.

*Discoloration.*—The general tonality at the end of the first day: Paler, less orange than at the beginning of the first day. At the end of the third day, Yellow Group 10C.

*Fragrance.*—Moderate.

Petals:

*Texture.*—Firm.

*Shape.*—Outer petals are round, notched; inner petals are oval.

*Form.*—Outer petals cupped; edges very slightly quilled.

*Arrangement.*—Imbricated (regularly arranged, shingle-like), sometimes a few central petals are tucked into the calyx, with a few small petaloids in the center.

*Persistence.*—Petals drop off cleanly before drying.

*Lastingness.*—On the plant: About 3 to 4 days. As a cut flower: About 3 days.

Reproductive parts:

*Anthers.*—Size: Medium. Quantity: Many. Color: Golden yellow. Arrangement: Tucked into calyx or partly so; mixed with petaloids.

*Filaments.*—Color: Golden yellow, sometimes pink blush at the base.

*Pollen.*—Color: Gold yellow.

*Styles.*—Color: Greenish white, sometimes with pink blush at the top.

*Stigmas.*—Color: Yellow: central stigmas/styles sometimes foliate.

Form: Shrub.

Growth: Vigorous.

Foliage: Number of leaflets on normal mid-stem leaves: 7.

*Size.*—About 19 cm long×13 cm wide.

*Quantity.*—Normal.

*Color.*—New foliage: Yellow-Green Group 144A with Red-Purple 59A blush on margins. Old foliage: Yellow-Green Group 147A.

Leaflets:

*Shape.*—Pointed oval.

*Texture.*—Upper side: Leathery.

*Edge.*—Serrated.

*Serration.*—Double.

*Petiole rachis.*—Color: Green; reddish at nodes.

*Petiole underside.*—1 to 3 prickles per internode.

*Stipules.*—About 2.5 cm long.

*Disease resistance.*—Resistant to mildew and black-spot under normal growing conditions at Albrighton, Wolverhampton, England.

Wood:

*New wood.*—Color: Medium green (faint blush). Bark: Smooth.

*Old wood.*—Color: Green. Bark: Smooth.

Prickles:

*Quantity.*—On main canes from base: Few to ordinary. On laterals from main canes: Very few.

*Form.*—Medium length, hooked downward.

*Color when young.*—Red, tips transparent.

*Position.*—Randomly distributed mostly on lower nodes of main stem.

Small Prickles:

*Quantity.*—On main stalks: None to few. On laterals: None.

*Color.*—Brown.

I claim:

1. A new and distinct variety of rose plant of the shrub class, substantially as herein shown and described, characterized particularly as to novelty by the unique combination of its full, double, orange/yellow flowers; repeat flowering; and bush growth.

* * * * *

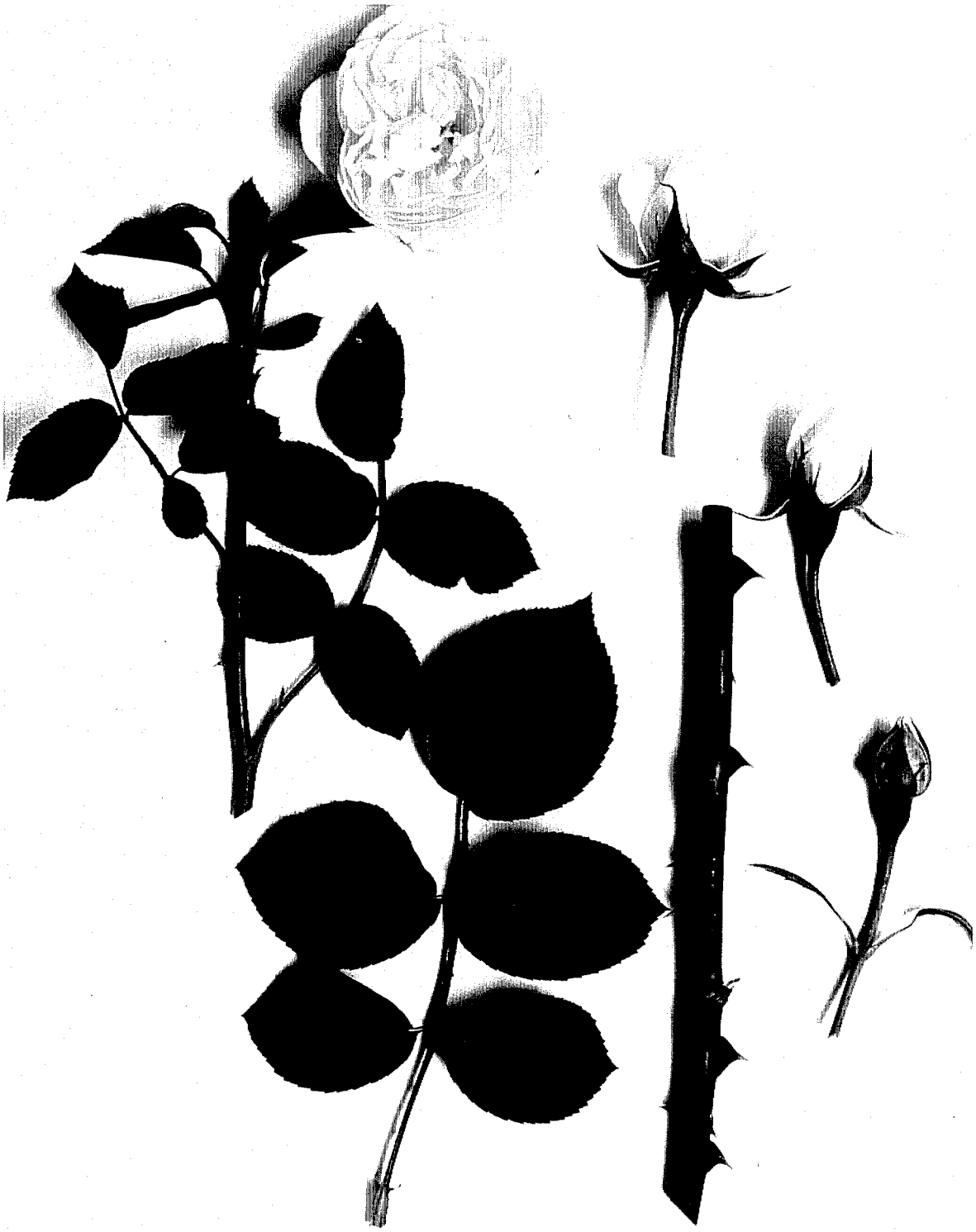
AUSPOLY

UNITED STATES PATENT AND TRADEMARK OFFICE

CERTIFICATE OF CORRECTION

PATENT NO. : PLANT 9,008

DATED : December 13, 1994

INVENTOR(S) : David C. H. Austin

It is certified that error appears in the above-indentified patent and that said Letters Patent is hereby corrected as shown below:

Column 1, line 45, "Jul. 1992" should read --July, 1992--.

Column 2, line 18, "14 mm long X8 to 9 mm wide." should read --14 mm long X8 to 9 mm wide. *Surface: Smooth*.--.

Column 2, line 19, "*Peduncle.-Surface Smooth Length: Averaging*" should read --*Peduncle*.-Length: Averaging--.

Column 2, line 20, "*about*" should read --about--.

Column 2, line 27, "stem." should read --stems:--.

Column 3, line 19, "Yellow:" should read --Yellow;--

Signed and Sealed this

Fourteenth Day of October, 1997

*Attest:*

*Attesting Officer*

Bruce Lehman

BRUCE LEHMAN

*Commissioner of Patents and Trademarks*